United States Patent
Kishi

(10) Patent No.: US 9,630,323 B2
(45) Date of Patent: Apr. 25, 2017

(54) OPERATION SUPPORT SYSTEM AND CONTROL METHOD OF OPERATION SUPPORT SYSTEM

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/718,404

(22) Filed: May 21, 2015

(65) Prior Publication Data
US 2015/0321355 A1 Nov. 12, 2015

Related U.S. Application Data

(63) Continuation of application No. PCT/JP13/82516, filed on Nov. 27, 203.
(Continued)

(51) Int. Cl.
*G06F 19/00* (2011.01)
*B25J 9/16* (2006.01)
(Continued)

(52) U.S. Cl.
CPC ............ *B25J 9/1697* (2013.01); *A61B 34/30* (2016.02); *A61B 34/37* (2016.02); *B25J 9/1643* (2013.01);
(Continued)

(58) Field of Classification Search
CPC combination set(s) only.
See application file for complete search history.

(56) References Cited

U.S. PATENT DOCUMENTS 5,321,353 A * 6/1994 Furness .................. B25J 9/1697
318/568.11
6,036,637 A * 3/2000 Kudo .................. A61B 1/00039
600/102
(Continued)

FOREIGN PATENT DOCUMENTS

JP S63-267177 A 11/1988
JP H02-310706 A 12/1990
(Continued)

OTHER PUBLICATIONS

International Search Report dated Mar. 11, 2014 issued in PCT/JP2013/082516.
(Continued)

*Primary Examiner* — Bhavesh V Amin
(74) *Attorney, Agent, or Firm* — Scully, Scott, Murphy & Presser, P.C.

(57) ABSTRACT

An operation support system performing treatment on a target tissue while observing using an image capturing unit, using a treatment unit installed at a distal end side of a manipulator, a distal end seen from a fixing end of the manipulator, includes: the manipulator having joints corresponding to degrees of freedom and including at least two redundant joints having a redundant relationship among the joints; an operating unit configured to provide operating information corresponding to the degrees of freedom; a positional relationship calculation unit calculating a switching positional relationship between the target tissue or the treatment unit and the image capturing unit; and a control unit controlling an operation of the joint according to the operating information. The control unit controls the manipulator using one redundant joint as a driving joint and the other redundant joints as a fixing joint based on the switching positional relationship.

13 Claims, 15 Drawing Sheets

Related U.S. Application Data

(60) Provisional application No. 61/731,802, filed on Nov. 30, 2012.

(51) Int. Cl.
*A61B 34/30* (2016.01)
*A61B 34/37* (2016.01)
*A61B 90/30* (2016.01)
*A61B 90/00* (2016.01)

(52) U.S. Cl.
CPC ............ *A61B 90/30* (2016.02); *A61B 90/361* (2016.02); *A61B 2034/306* (2016.02); *G05B 2219/39425* (2013.01); *Y10S 901/02* (2013.01)

(56) References Cited

U.S. PATENT DOCUMENTS

| | | | | |
|---|---|---|---|---|
| 6,645,196 | B1* | 11/2003 | Nixon | B25J 9/1664 128/898 |
| 6,786,896 | B1 | 9/2004 | Madhani et al. | |
| 8,079,950 | B2* | 12/2011 | Stern | A61B 1/00188 600/109 |
| 2002/0128552 | A1* | 9/2002 | Nowlin | A61B 34/70 600/427 |
| 2003/0114962 | A1* | 6/2003 | Niemeyer | A61B 1/00149 700/245 |
| 2007/0013336 | A1 | 1/2007 | Nowlin et al. | |
| 2007/0083098 | A1* | 4/2007 | Stern | A61B 1/00188 600/407 |
| 2008/0065109 | A1* | 3/2008 | Larkin | A61B 1/00087 606/130 |
| 2008/0202274 | A1 | 8/2008 | Stuart | |
| 2009/0036902 | A1* | 2/2009 | DiMaio | A61B 19/2203 606/130 |
| 2010/0204713 | A1 | 8/2010 | Morales | |
| 2011/0015649 | A1* | 1/2011 | Anvari | A61B 34/20 606/130 |
| 2011/0245844 | A1* | 10/2011 | Jinno | A61B 34/37 606/130 |
| 2011/0301616 | A1* | 12/2011 | Sanchez | A61B 19/2203 606/130 |
| 2012/0059519 | A1* | 3/2012 | Kishi | B25J 3/04 700/264 |
| 2012/0143353 | A1 | 6/2012 | Kishi | |

FOREIGN PATENT DOCUMENTS

| | | |
|---|---|---|
| JP | 08-505091 A | 6/1996 |
| JP | 2011-206312 A | 10/2011 |
| JP | 2012-050888 A | 3/2012 |
| JP | 2012-055996 A | 3/2012 |
| JP | 2012-131014 A | 7/2012 |
| WO | 94/15758 A1 | 7/1994 |
| WO | 2007/030173 A1 | 3/2007 |

OTHER PUBLICATIONS

Extended Supplementary European Search Report dated Jul. 6, 2016 in related European Application No. 13 85 8865.2.

* cited by examiner

OPERATION SUPPORT SYSTEM AND CONTROL METHOD OF OPERATION SUPPORT SYSTEM

This application is a continuation application based on PCT Patent Application No. PCT/JP2013/082516, filed Nov. 27, 2013, whose priority is claimed on U.S. Provisional Patent Application No. 61/731,802, filed Nov. 30, 2012. The contents of both the PCT Patent Application and the U.S. Provisional Patent Application are incorporated herein by reference.

BACKGROUND OF THE INVENTION

Field of the Invention

The present invention relates to an operation support system having a redundant joint and a control method of an operation support system capable of controlling the operation support system.

Description of Related Art

In recent times, in attempts to conserve manpower in medical facilities, research on medical treatment by robots has been performed. In particular, in fields of surgery, in an operation support system for performing treatment of a patient by a manipulator having multiple degrees of freedom (multiple joints), various proposals have been set forth. In such an operation support system, it is known that a manipulator that comes in direct contact with a body cavity of a patient can be remotely operated by a remote operation apparatus.

Here, when a needle-hooking operation, which is particularly difficult in an operation with an endoscope, is performed using the operation support system, a needle is hooked while rolling a gripper attached to a distal end of a manipulator. Here, in a manipulator in which a roll axis joint is not provided at a distal end thereof, another joint is cooperatively operated according to rolling to roll the gripper attached to the distal end. In this case, a plurality of joints may be operated to collide with surrounding internal organs or the like.

On the other hand, as the so-called redundant joint is installed at the distal end section, for example, a master-slave manipulator capable of position and orientation decision of the distal end only is disclosed in Japanese Unexamined Patent Application, First Publication No. S63-267177. In addition, in the redundant joint, a joint having a motion shaft, which is one of a rotary shaft and a linear moving shaft, is provided, and in an initial state, the motion shaft of the joint is parallel, and another joint having the motion shaft, which is the same kind of a rotary shaft and a linear moving shaft, is disposed in the manipulator.

SUMMARY OF THE INVENTION

According to a first aspect of the present invention, an operation support system configured to perform treatment on a target tissue, which is a treatment target, while observing by using an image capturing unit, using a treatment unit installed at a distal end side of a manipulator, which is a distal end when seen from a fixing end of the manipulator, includes: the manipulator having a plurality of joints corresponding to a plurality of degrees of freedom and including at least two redundant joints having a redundant relationship among the plurality of joints; an operating unit configured to provide operating information corresponding to the plurality of degrees of freedom; a positional relationship calculation unit configured to calculate a switching positional relationship between the target tissue or the treatment unit and the image capturing unit; and a control unit configured to control an operation of the joint according to the operating information. The control unit controls the manipulator using one of the at least two redundant joints as a driving joint and the other redundant joints of the at least two redundant joints as a fixing joint based on the switching positional relationship.

According to a second aspect of the present invention, in the operation support system according to the first aspect, the switching positional relationship may represent a distance between the target tissue or the treatment unit and the image capturing unit. The control unit may use the joint closest to a distal end of the manipulator of the at least two redundant joints as the driving joint when the switching positional relationship is equal to or less than a threshold, and the control unit may use the joint farthest from the distal end of the manipulator of the at least two redundant joints as the driving joint when the switching positional relationship is larger than the threshold.

According to a third aspect of the present invention, in the operation support system according to the first aspect, the positional relationship calculation unit may include: an image capturing unit detection unit configured to detect a position of the image capturing unit; and a treatment unit detection unit configured to detect a position of the treatment unit. The positional relationship calculation unit may be configured to calculate a distance between the treatment unit and the image capturing unit as the switching positional relationship based on the detected position of the image capturing unit and the detected position of the treatment unit.

According to a fourth aspect of the present invention, the operation support system according to the third aspect may further include the image capturing unit capable of acquiring an image.

According to a fifth aspect of the present invention, in the operation support system according to the third aspect, the positional relationship calculation unit may be configured to calculate the switching distance only when the treatment unit is disposed in a field of vision of the image capturing unit.

According to a sixth aspect of the present invention, in the operation support system according to the first aspect, the positional relationship calculation unit may be configured to calculate a distance between the treatment unit and the image capturing unit as the switching positional relationship based on the image obtained by photographing the treatment unit and acquired by the image capturing unit.

According to a seventh aspect of the present invention, in the operation support system according to the first aspect, the image capturing unit may be able to acquire a first image and a second image obtained by photographing the target tissue from different oblique directions. The positional relationship calculation unit may be configured to calculate a distance between the target tissue and the image capturing unit as the switching distance based on the acquired first and second images.

According to an eighth aspect of the present invention, a control method of an operation support system configured to control the operation support system including a manipulator having a plurality of joints corresponding to a plurality of degrees of freedom and including at least two redundant joints having a redundant relationship among the plurality of joints, includes: calculating a switching positional relationship between a target tissue treated using a treatment unit installed at the manipulator or the treatment unit and the image capturing unit; and controlling the manipulator based

DETAILED DESCRIPTION OF THE INVENTION

First Preferred Embodiment

Hereinafter, an operation support system in accordance with a first preferred embodiment of the present invention will be described with reference to FIGS. 1 to 8.

Figure 1:
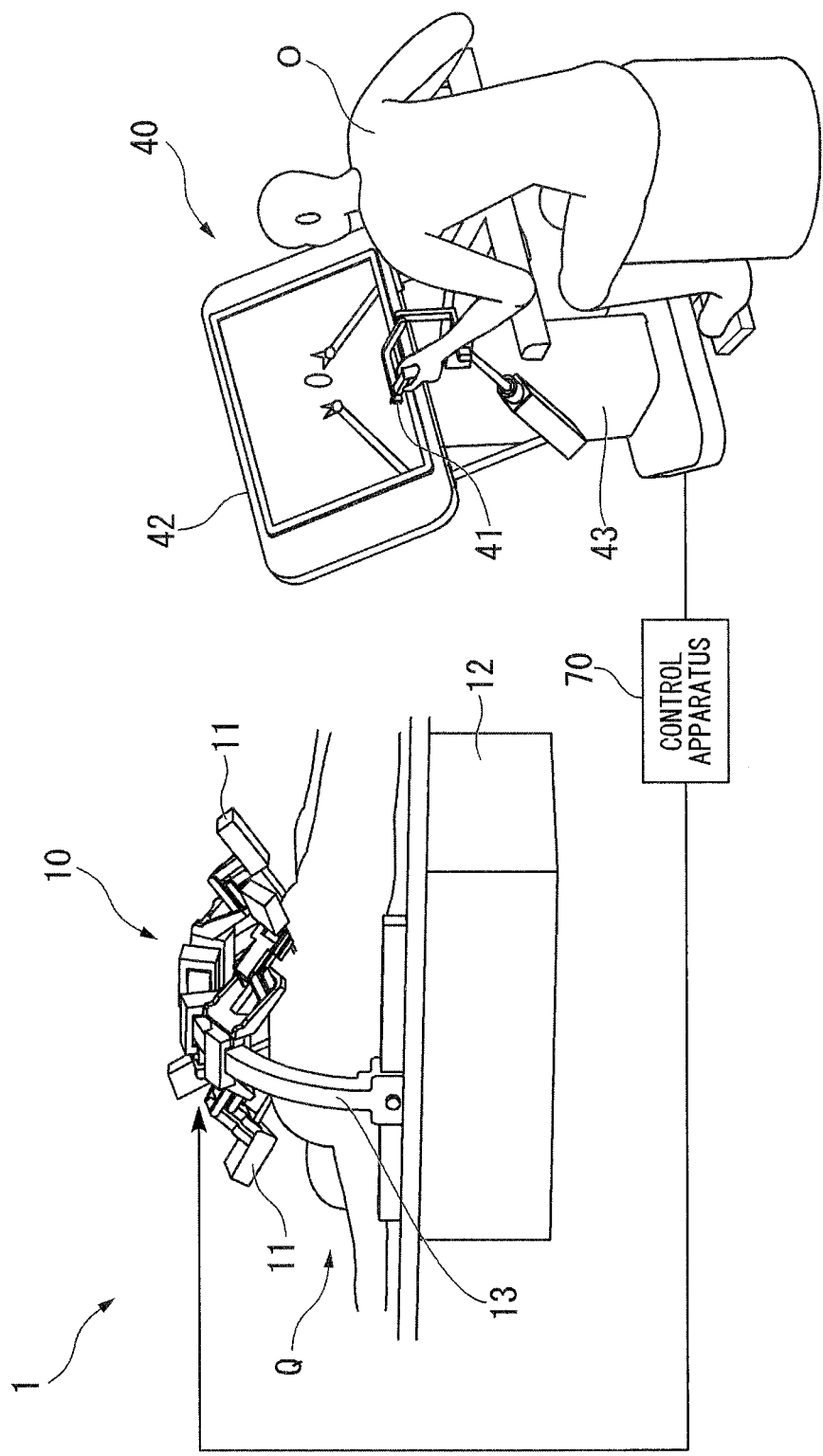
FIG. 1 is a general view showing an operation support system in accordance with a first preferred embodiment of the present invention

As shown in FIG. 1, an operation support system 1 in accordance with the first preferred embodiment includes a slave apparatus 10 having a plurality of slave manipulators (manipulators) 11, a master apparatus (an operating unit) 40 configured to apply operating information, and a control apparatus 70 configured to control the slave manipulators 11 according to the operating information.

Figure 2:
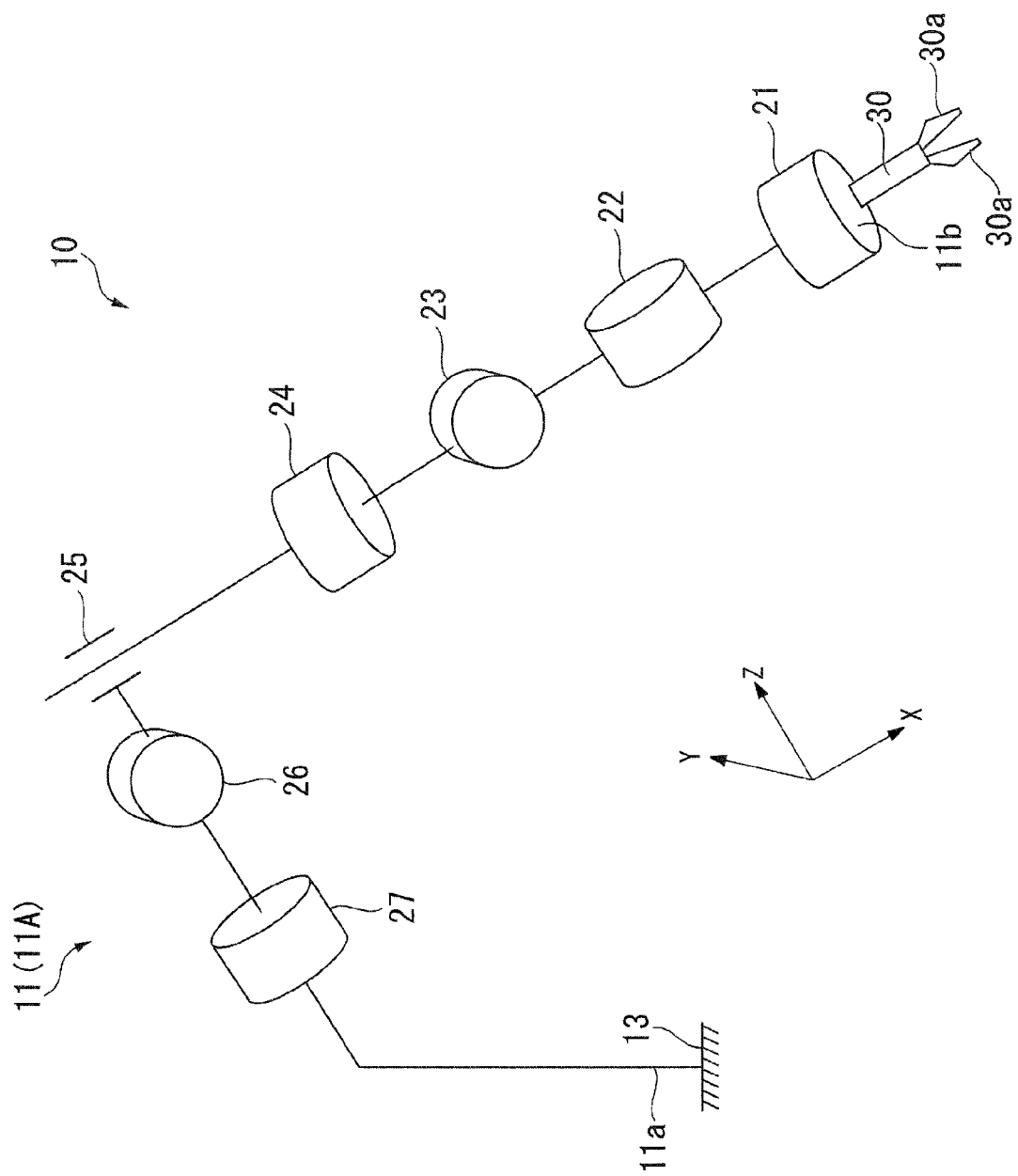
FIG. 2 is a view schematically showing one of slave manipulators of the operation support system in accordance with the first preferred embodiment of the present invention.

As shown in FIGS. 1 and 2, the slave apparatus 10 has an operating table 12, and the plurality of slave manipulators 11 having fixing ends 11a fixed to a frame 13 installed at the operating table 12. In addition, since the slave manipulators 11 have the same configuration, hereinafter, among the plurality of slave manipulators 11, a slave manipulator 11A to which a forceps 30 (to be described below) is attached will be described.

In the preferred embodiment, as shown in FIG. 2, the slave manipulator 11A has joints 21 to 27 corresponding to 7 degrees of freedom, and the joints 21 to 27 are driven according to operating information from the master apparatus 40. In the slave manipulator 11A, the seven joints 21 to 27 are disposed such that the joint 27 is disposed near the fixing end 11a.

Among these joints 21 to 27, the joint 21 and the joint 24 are joints rotated about a roll axis (an X axis). That is, motion shafts of the joints 21 and 24 are rotary shafts parallel to the X axis. The joint 22 and the joint 27 are joints rotated about a yaw axis (a Z axis), and motion shafts of the joints 22 and 27 are rotary shafts parallel to the Z axis. The joint 23 and the joint 26 are joints rotated about a pitch axis (a Y axis), and motion shafts of the joints 23 and 26 are rotary shafts parallel to the Y axis.

In addition, the joint 25 is a joint expanded and contracted along the roll axis.

The motion shafts of the joints 21 to 25 are disposed on the same straight line. The motion shafts of the joints 26 and 27 are disposed on the same straight line. Since the motion shafts of the joints 21 and 24 are the rotary shafts and the motion shafts are parallel to each other in an initial state shown in FIG. 2, the joints are redundant joints having a redundant relationship.

A forceps (a treatment unit) 30 is attached to a distal end 11b of the slave manipulator 11A. A wire motor 30b (see FIG. 3) is connected to the pair of forceps pieces 30a installed at a distal end section of the forceps 30 via an operation wire (not shown). As the wire motor 30b is driven to advance or retreat the operation wire, the distal end sections of the pair of forceps pieces 30a can approach or separate from each other. In this example, the forceps 30 is formed in a rod shape.

Figure 3:
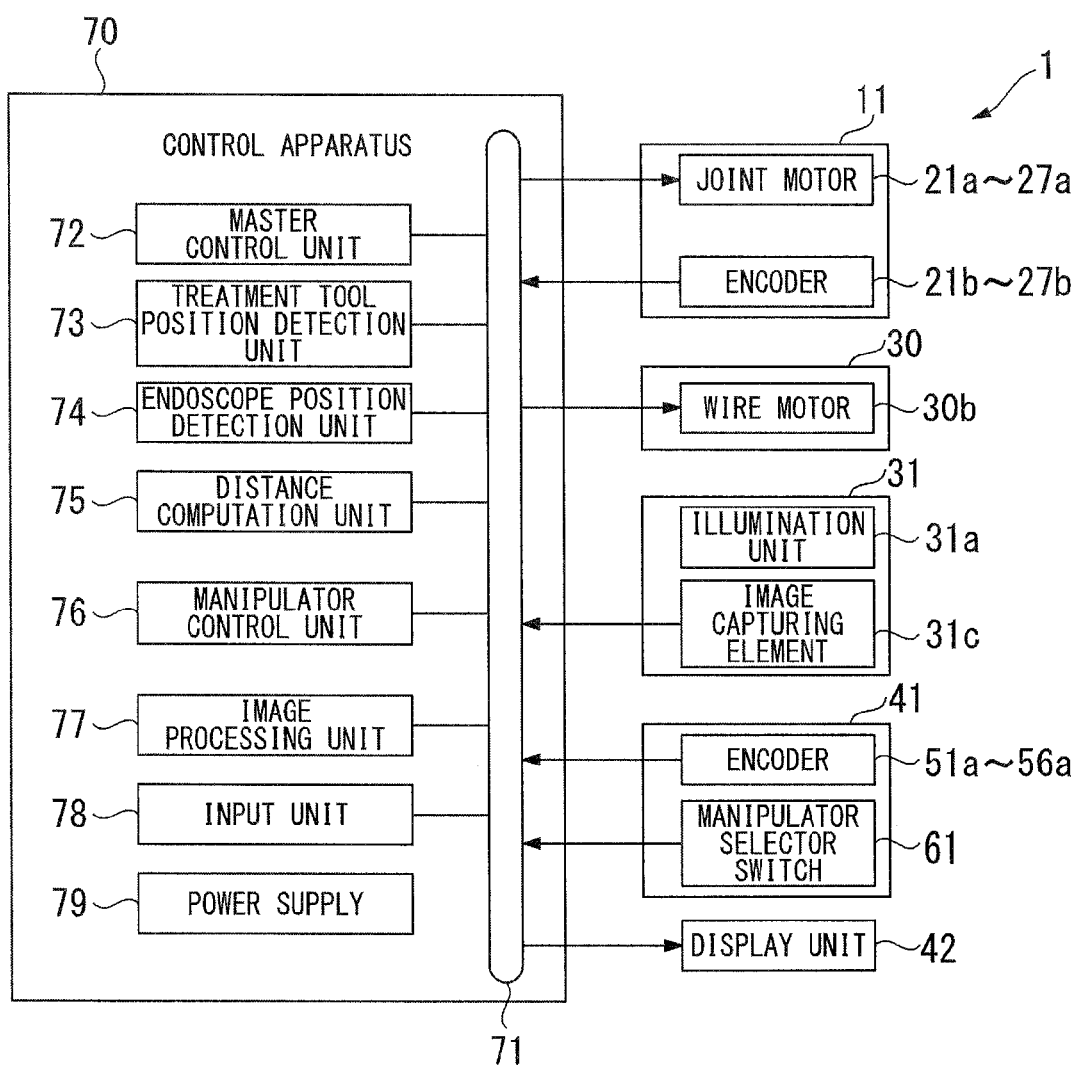
FIG. 3 is a block diagram showing the operation support system in accordance with the first preferred embodiment of the present invention.

As shown in FIG. 3, a joint motor 21a configured to drive the joint 21 and an encoder 21b configured to detect a rotation angle of the joint 21 are installed at the joint 21. Like the joint 21, joint motors 22a to 24a, 26a and 27a and encoders 22b to 24b, 26b and 27b are also installed at the joints 22 to 24, 26 and 27, respectively. A joint motor 25a configured to drive the joint 25 and an encoder 25b configured to detect expansion and contraction amounts of the joint 25 are installed at the joint 25.

These joints 21 to 27 can be independently driven by driving the joint motors 21a to 27a. Detection results detected by the encoders 21b to 27b are output to the control apparatus 70.

As the joints 22 to 27 shown in FIG. 2 are cooperatively driven, in the slave manipulator 11A, 3 degrees of freedom of a position and 3 degrees of freedom of an orientation of the forceps 30 of the distal end of the slave manipulator 11A, which is a distal end when seen from the fixing end 11a, are realized. In addition, in addition to these joints 22 to 27, in the slave manipulator 11A, the joint 21 configured to roll the forceps 30 of the distal end is installed as a redundant joint. According to the above-mentioned configuration, for example, when the forceps 30 of the distal end of the slave manipulator 11A is rolled, it is possible to select whether the joint 24, which is a joint far from the forceps 30 of the distal end, is rolled or the joint 21, which is a joint near the forceps 30 of the distal end, is rolled in a timely manner. In the preferred embodiment, as the joint 21 and the joint 24 having a redundant relationship are not simultaneously driven, inverse kinematics calculation is simplified.

Figure 4:
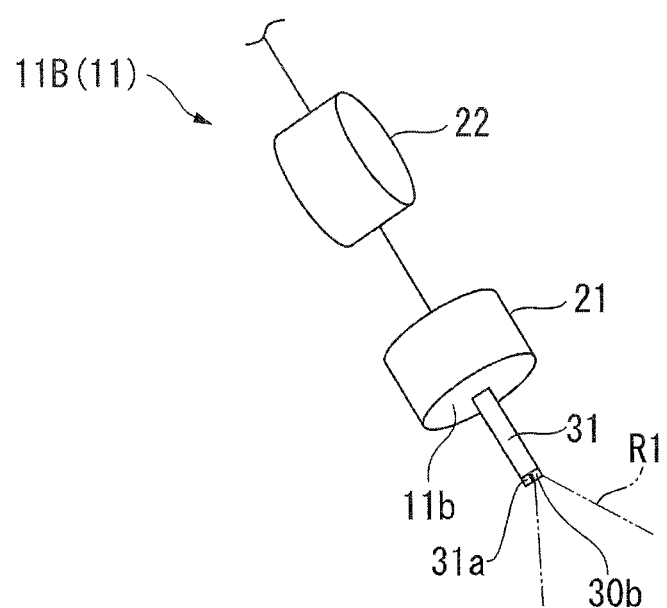
FIG. 4 is a view schematically showing a distal end side of another one of the slave manipulators of the operation support system in accordance with the first preferred embodiment of the present invention.

An endoscope (an image capturing unit) 31 is attached to a distal end 11b of a slave manipulator 11B shown in FIG. 4, which is one of the slave manipulators 11 other than the slave manipulator 11A. An illumination unit 31a having an LED or the like and an optical unit 31b are installed at the distal end section of the endoscope 31 in a state exposed to the outside. An image capturing element 31c (see FIG. 3) such as a CCD or the like is installed closer to a proximal end side of the endoscope 31 than the optical unit 31b. The optical unit 31b images an image of a target in a field of vision R1 defined in front of the optical unit 31b on a light receiving surface (not shown) of an image capturing element 31c. The image capturing element 31c acquires an image by a picture on a light receiving surface, and converts the image into a signal to output the signal to the control apparatus 70.

As shown in FIG. 1, the master apparatus 40 has an operating unit 41 and a display unit 42.

Figure 5:
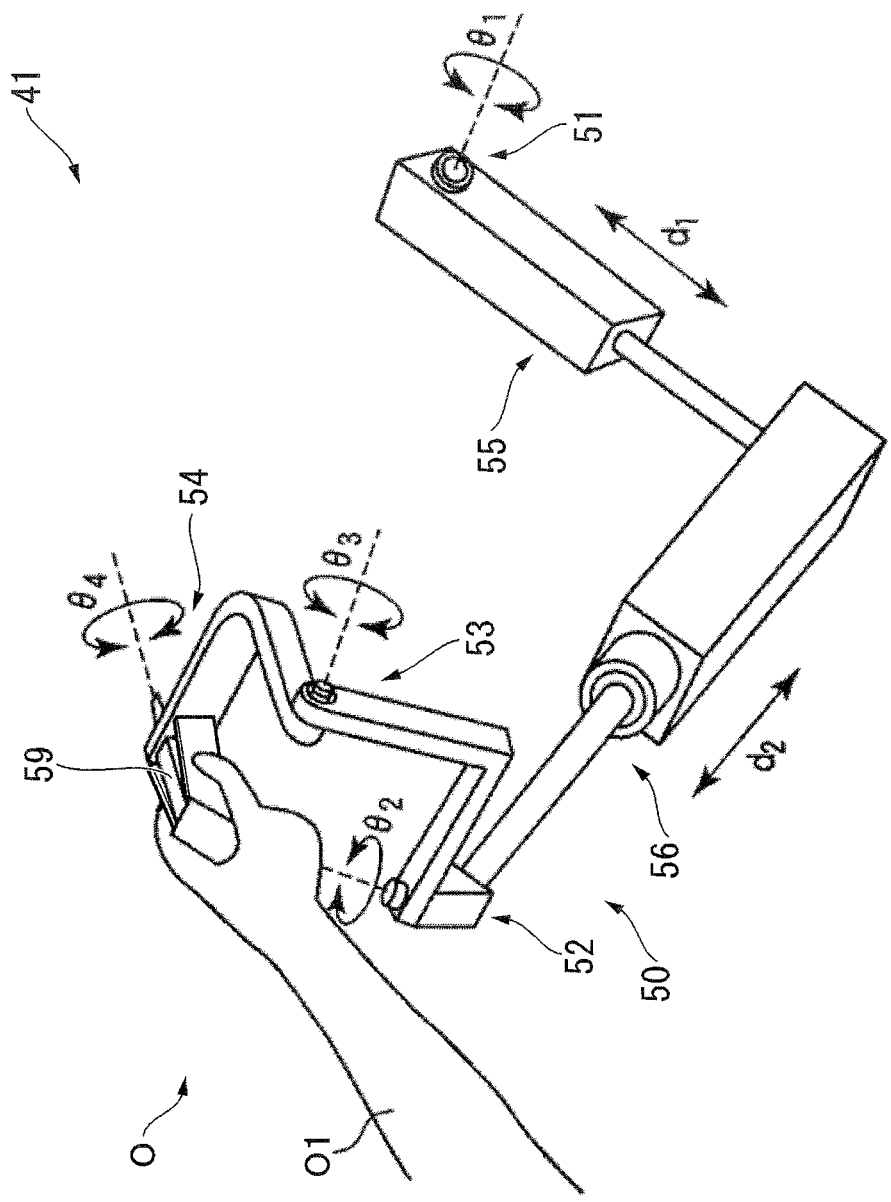
FIG. 5 is a perspective view showing an operating unit of the operation support system in accordance with the first preferred embodiment of the present invention.

For example, as shown in FIG. 5, the operating unit 41 has a driving unit 50 including driving shafts 51 to 54 constituted by a rotary mechanism and driving shafts 55 and 56 constituted by a linear motion mechanism. A support frame 43 configured to support the operating unit 41 and the display unit 42 is fixed to a proximal end section of the driving unit 50 (see FIG. 1). A grip 59 is installed at a distal end section (gripped by an arm O1 of an operator O such as a practitioner or the like) of the operating unit 41.

In such a configuration, as the operator O moves or rotates the operating unit 41 while gripping the grip 59, the driving shafts 51 to 56 that constitute the operating unit 41 are driven. The driving amounts (a rotation angle in the case of the rotary mechanism or a displacement amount in the case of the linear motion mechanism) of the driving shafts 51 to 56 are detected by encoders 51a to 56a (see FIG. 3) installed at the driving shafts 51 to 56, respectively, and the detection signals of the encoders 51a to 56a are output to the control apparatus 70 as signals (operation signals) showing operating information of the operating unit 41 for instructing a position and an orientation of the forceps 30 of the distal end of the slave manipulator 11 of the slave apparatus 10.

The operating unit 41 of the preferred embodiment has six driving shafts and outputs six operation signals θ1, d1, d2, θ2, θ3 and θ4 of the encoders 51a to 56a obtained by moving the six driving shafts 51 to 56. A master control unit 72 (to be described below) of the control apparatus 70 calculates position/orientation instruction signals to the slave manipulator 11 using these values.

A manipulator selector switch 61 configured to switch the slave manipulator 11 controlled by the operating unit 41 is installed at the operating unit 41 (see FIG. 3). Further, while not shown, a switch or the like configured to drive the wire motor 30b or the like is installed at the operating unit 41.

For example, the display unit 42 is constituted by a liquid crystal display and displays an image based on the image signal input from the control apparatus 70.

As shown in FIG. 3, the control apparatus 70 has the master control unit 72 connected to a bus 71, a treatment tool position detection unit 73, an endoscope position detection unit 74, a distance computation unit 75, a manipulator control unit (a control unit) 76, an image processing unit 77, an input unit 78 and a power supply 79. The joint motors 21a to 27a of the slave manipulator 11, the encoders 21b to 27b, the wire motor 30b of the forceps 30, the image capturing element 31c of the endoscope 31, the encoders 51a to 56a of the operating unit 41, the manipulator selector switch 61 and the display unit 42 are connected to the bus 71.

Each of the master control unit 72, the treatment tool position detection unit 73, the endoscope position detection unit 74, the distance computation unit 75, the manipulator control unit 76, and the image processing unit 77 is constituted by a computing device, a memory, a control program, and so on.

The master control unit 72 calculates instruction values of the position and the orientation of the forceps 30 of the distal end of the slave manipulator 11 according to the operation signals from the master apparatus 40 corresponding to the 6 degrees of freedom. Then, the calculated instruction value is output to the manipulator control unit 76.

A length between the neighboring joints of the slave manipulator 11A, a length of the forceps 30, and so on, are stored in the treatment tool position detection unit 73. The treatment tool position detection unit 73 detects a position of the distal end section of the forceps 30 based on a detection result input from the encoders 21b to 27b of the slave manipulator 11A, the above-mentioned stored length, and so on. In addition, a treatment unit detection unit is constituted by the encoders 21b to 27b of the slave manipulator 11A and the treatment tool position detection unit 73.

A length between the neighboring joints of the slave manipulator 11B, a length of the endoscope 31, and so on, are stored in the endoscope position detection unit 74. The endoscope position detection unit 74 detects the position and the orientation of the distal end section of the endoscope 31 based on detection results input from the encoders 21b to 27b of the slave manipulator 11B and the above-mentioned stored length. In addition, an image capturing unit detection unit is constituted by the encoders 21b to 27b of the slave manipulator 11B and the endoscope position detection unit 74.

Figure 6:
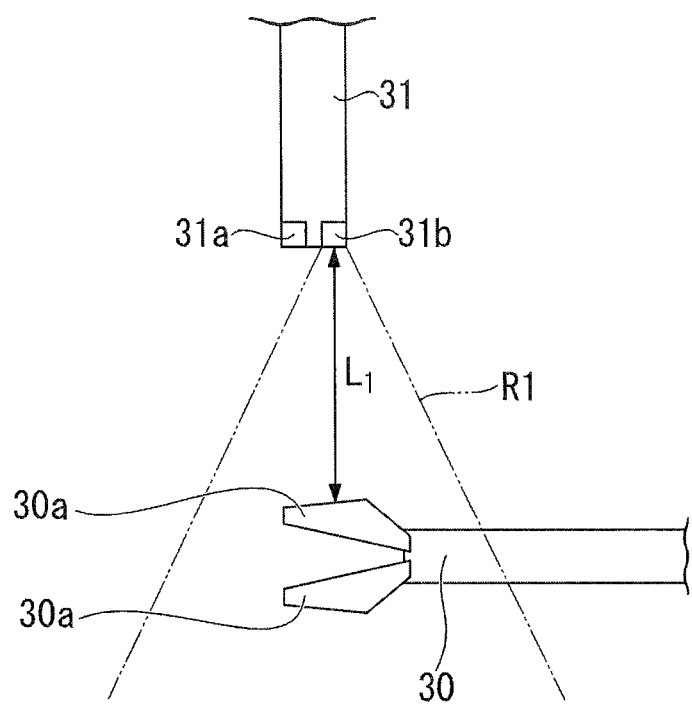
FIG. 6 is a view for describing a switching distance measured by a control apparatus of the operation support system in accordance with the first preferred embodiment of the present invention.

Disposition of the field of vision R1 or the like in the endoscope 31 is stored in the distance computation unit 75. The distance computation unit 75 calculates a switching distance (switching positional relationship) L1, which is a distance between the distal end section of the forceps 30 and the distal end section of the endoscope 31 spread in a substantially conical shape along a central axis of the field of vision R1 as shown in FIG. 6, from a position of the distal end section of the forceps 30 detected by the treatment tool position detection unit 73 and a position of the distal end section of the endoscope 31 detected by the endoscope position detection unit 74. A positional relationship calculation unit is constituted by the image capturing unit detection unit, the treatment unit detection unit, and the distance computation unit 75. In addition, the distance computation unit 75 can detect whether the distal end section of the forceps 30 is disposed in the field of vision R1 of the endoscope 31 or not from the position of the distal end section of the forceps 30 and the position and the orientation of the distal end section of the endoscope 31.

The manipulator control unit 76 calculates driving amounts of the joints 21 to 27 of the slave manipulator 11 needed to coincide with the instruction values of the position and the orientation of the forceps 30 of the distal end of the slave manipulator 11 through inverse kinematics calculation based on the instruction values of the position and the orientation from the master apparatus 40.

In addition, the manipulator control unit 76 controls to select and drive one of the joints 21 and 24 and fix the other joint based on the switching distance L1. More specifically, the manipulator control unit 76 selects and drives the joint 21 close to the forceps 30 of the distal end of the slave manipulator 11, of the joints 21 and 24 of the slave manipulator 11, and fixes the joint 24 far from the forceps 30 of the distal end, when the switching distance L1 is a predetermined threshold or less. That is, the manipulator control unit 76 controls the slave manipulator 11 using the joint 21 as a driving joint and the joint 24 as a fixing joint. Meanwhile, when the switching distance L1 is larger than the threshold, the manipulator control unit 76 selects and drives the joint 24 and fixes the joint 21. The threshold may be set to, for example, 20 mm or the like, according to content of the procedure, a kind of a used treatment tool (treatment unit), or the like.

The image processing unit 77 converts the image acquired by the endoscope 31 shown in FIG. 3 into an image signal and outputs the image signal to the display unit 42.

The input unit 78 is, for example, a keyboard, and disposed in the vicinity of the slave apparatus 10. An instruction input from the input unit 78 by an assistant is output to the master control unit 72 or the like.

The power supply 79 supplies power input from the outside to the slave manipulator 11, the master apparatus 40, the master control unit 72, and so on.

Next, a procedure using the operation support system 1 of the preferred embodiment having the above-mentioned configuration will be described. Hereinafter, a case in which a treatment tool is introduced into the body cavity of the patient and a target tissue is sutured will be exemplarily described.

The assistant lays a patient Q on the operating table 12 as shown in FIG. 1, and performs appropriate processing such as sterilization, anesthesia, and so on. When the assistant operates the input unit 78 to start the operation support system 1, power is supplied from the power supply 79 to the slave manipulator 11, the master apparatus 40, the master control unit 72, and so on.

Figure 7:
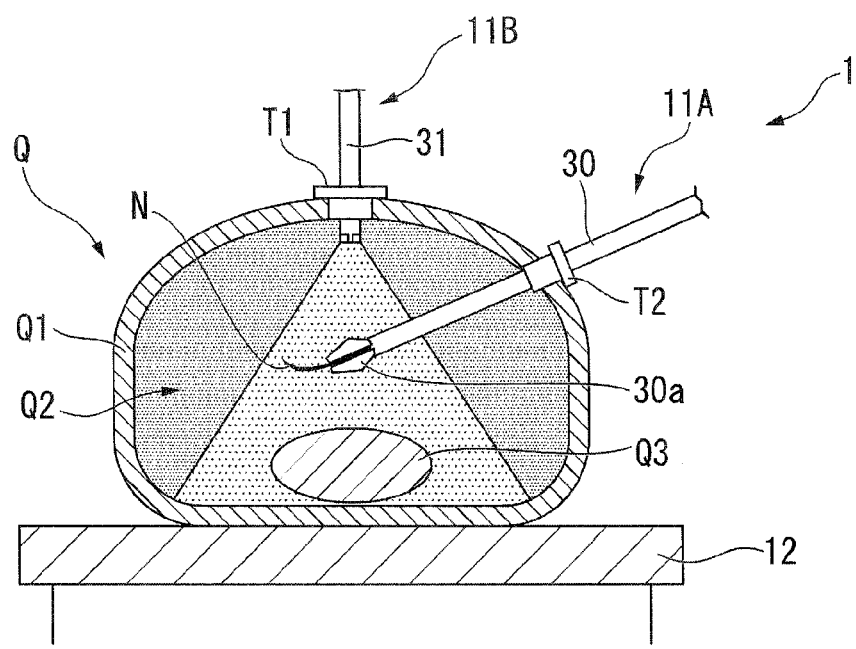
FIG. 7 is a view for describing a control method of an operation support system in accordance with the first preferred embodiment of the present invention.

As shown in FIG. 7, trocars T1 and T2 are attached to a body wall Q1 of the patient Q to be directed in different directions.

Power is supplied to the illumination unit 31a to illuminate ahead of the endoscope 31, and an image acquired by the image capturing element 31c is displayed on the display unit 42. In a state in which the operator O observes the image of the display unit 42, the assistant introduces the endoscope 31 into a body cavity Q2 of the patient Q through the trocar T1. In addition, introduction of the endoscope 31 may be performed by control of the master apparatus 40.

The operator O operates the operating unit 41 and inputs an appropriate threshold corresponding to content or the like of the procedure. The input threshold is stored in the manipulator control unit 76. The operating unit 41 is operated to drive the wire motor 30b of the forceps 30, and a curved needle N for suturing is gripped between the pair of forceps pieces 30a at the outside of the body of the patient Q.

Figure 8:
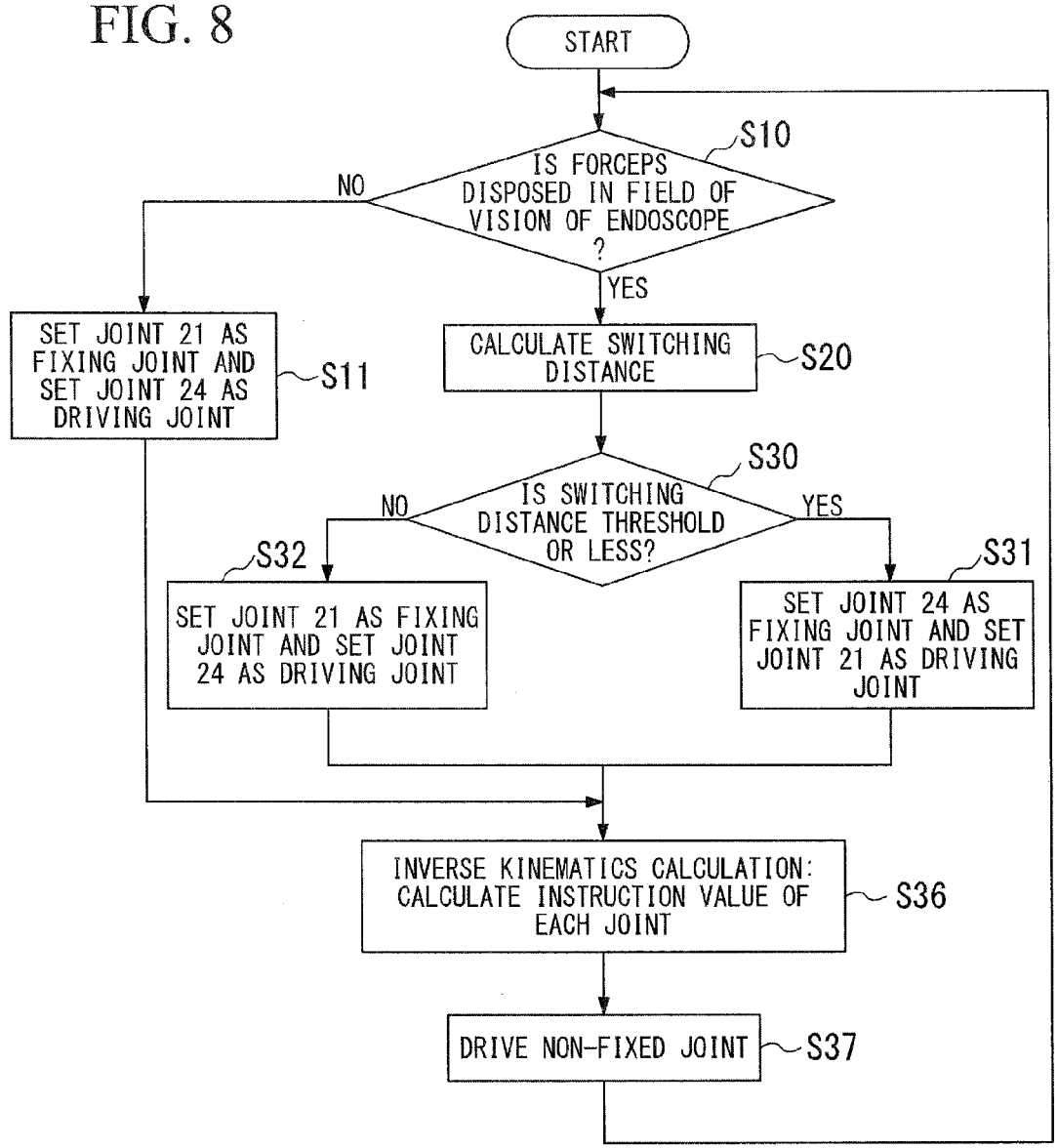
FIG. 8 is a flowchart showing the control method of the operation support system in accordance with the first preferred embodiment of the present invention.

The manipulator selector switch 61 is operated to be switched such that the slave manipulator 11A is controlled by the operating unit 41. Here, the operation support system 1 of the preferred embodiment is controlled as follows. FIG. 8 is a flowchart showing a control method of the operation support system 1.

First, in step S10, the treatment tool position detection unit 73 detects a position of the distal end section of the forceps 30, and the endoscope position detection unit 74 detects the position and the orientation of the distal end section of the endoscope 31. The distance computation unit 75 detects whether the distal end section of the forceps 30 is disposed in the field of vision R1 of the endoscope 31 or not, from the detected position of the distal end section of the forceps 30 and the detected position and orientation of the distal end section of the endoscope 31. When the distance computation unit 75 determines that the distal end section of the forceps 30 is disposed in the field of vision R1 (YES), step S20 is performed.

When the distance computation unit 75 determines that the distal end section of the forceps 30 is not disposed in the field of vision R1 (NO), step S11 is performed. In step S11, the joint 21 is set as a fixing joint and the joint 24 is set as a driving joint. Then, step S36 is performed.

In the above-mentioned step S20, the distance computation unit 75 calculates the switching distance L1 from the position of the distal end section of the forceps 30 and the position of the distal end section of the endoscope 31, which are detected in step S10 performed just before. That is, the distance computation unit 75 calculates the switching distance L1 only when the distal end section of the forceps 30 is disposed in the field of vision R1 of the endoscope 31. Then, step S30 is performed.

In step S30, the manipulator control unit 76 determines whether or not the switching distance L1 is the threshold or less. When the switching distance L1 is the threshold or less (YES), step S31 is performed. In step S31, the joint 24 is set as a fixing joint and the joint 21 is set as a driving joint. Then, step S36 is performed.

Meanwhile, in step S30, when the manipulator control unit 76 determines that the switching distance L1 is not the threshold or less (NO), step S32 is performed. In step S32, the joint 21 is set as a fixing joint and the joint 24 is set as a driving joint. Then, step S36 is performed.

Next, in step S36, the manipulator control unit 76 calculates driving amounts of the joints 21 to 27 of the slave manipulator 11A needed for coincidence of the position and the orientation of the forceps 30 of the distal end of the slave manipulator 11A with the instruction values through inverse kinematics calculation, based on the instruction values of the position and the orientation received from the master control unit 72 and joint information set as the fixing joint and the driving joint in steps S31 and 32. Further, the instruction values with respect to each of the joints 21 to 27 are determined.

Next, in step S37, the manipulator control unit 76 drives the joints 21 to 27 of the slave manipulator 11A according to the instruction values of the joints 21 to 27 obtained in step S36. However, the joint set to be fixed in step S11, 31 or 32 is not driven in a fixed state. Then, step S10 is performed.

Steps S10 to 37 are repeated at each predetermined time Δt, for example, 1 millisecond. That is, setting any one of the joints 21 and 24 as the fixing joint may be automatically varied every moment. When the manipulator selector switch 61 is operated to control another slave manipulator 11 different from the slave manipulator 11A in the operating unit 41, this flow is forcedly terminated.

In this way, as steps S10 to 37 are performed, when the distal end section of the forceps 30 is disposed outside the field of vision R1 of the endoscope 31, and when the distal end section of the forceps 30 is disposed in the field of vision R1 of the endoscope 31 so that the switching distance L1 is relatively long, the joint 21 is fixed at a place close to the forceps 30 of the distal end of the slave manipulator 11A. Meanwhile, when the distal end section of the forceps 30 is disposed in the field of vision R1 of the endoscope 31 and further the switching distance L1 is relatively short, the joint 24 is fixed at a place far from the forceps 30 of the distal end of the slave manipulator 11A.

The operator O operates the operating unit 41 to introduce the forceps 30 of the slave manipulator 11A into the body cavity Q2 through the trocar T2 as shown in FIG. 7 while observing the image displayed on the display unit 42. Then, the distal end section of the forceps 30 approaches a target tissue Q3 to be treated.

In general, in the needle-hooking operation using the curved needle N, the curved needle N is hooked to the target tissue Q3 while rolling the forceps 30 attached to the forceps 30 of the distal end of the slave manipulator 11A. As described above, the slave manipulator 11A controls the position and the orientation of the forceps 30 while cooperatively operating the seven joints 21 to 27. Here, when the joint 24 far from the forceps 30, i.e., far from the forceps 30 of the distal end of the slave manipulator 11A, is rolled, the forceps 30 is also rolled, but the joints 21 to 23 closer to the distal end than the joint 24 are also largely operated, and these joints 21 to 23 or the like may collide with surrounding tissues or the like.

For this reason, when a rolling operation such as the needle-hooking operation is mainly needed, the joint 21, which is a joint near the forceps 30 of the distal end of the slave manipulator 11A, may be rolled such that the other joints are not unnecessarily operated. In this case, the joint 24 may be set as a fixing joint. The switching distance L1 is relatively short, the distal end section of the forceps 30 is largely displayed in the field of vision R1 of the endoscope 31, and a state of a proximal end side of the slave manipulator 11A cannot be easily recognized in the field of vision R1 of the endoscope 31. However, since the joints 21 to 27 are controlled not to be unnecessarily operated, there is no problem.

When the joint 24 is set as a fixing joint, since an obtained range of the position and the orientation of the forceps 30 of the distal end of the slave manipulator 11A is largely limited, the joint 24 may be driven to be rolled in the case of the operation in which rotation is needed in addition to the rolling. In this case, the joint 21 may be set as a fixing joint. Since the switching distance L1 is relatively large and a wide range of the distal end side of the slave manipulator 11A is displayed in the field of vision R1 of the endoscope 31, the operator O can easily recognize the operation even when the slave manipulator 11A is largely operated, enabling easy countermeasures.

In this way, while the slave manipulator 11A of the preferred embodiment includes the joints 21 to 27 corresponding to the 7 degrees of freedom, one joint is fixed and the other six joints are operated regardless of the value of the switching distance L1. For this reason, rather than setting the driving amounts of all seven of the joints with respect to 6 degrees of freedom of the position and the orientation as unknown amounts, as inverse kinematics calculation is performed with respect to the six independent joints, a problem of redundancy can be avoided and the inverse kinematics calculation can be simplified.

After the target tissue Q3 is sutured using the curved needle N, the forceps 30 is extracted from the trocar T2 and the endoscope 31 is extracted from the trocar T1.

Appropriate treatments such as extraction of the trocars T1 and T2 from the body wall Q1 of the patient Q and suturing of an opening of the body wall Q1 are performed, terminating a series of procedures.

In general, in the case of the operation support system having the redundant joint installed at the distal end shown in Japanese Unexamined Patent Application, First Publication No. S63-267177 or the like, the inverse kinematics calculation for calculating the driving amounts of the joints of the manipulator is complicated according to the operating information from the operating unit. In this case, the degree of freedom of the manipulator coincides with the degree of freedom of the operating unit because, for example, the redundant joint is temporarily fixed, and the inverse kinematics calculation can be simplified when the joints of the manipulator correspond one to one.

However, switching of the redundant joint fixed by the operator increases a burden to the operator during the procedure.

On the other hand, according to the operation support system 1 and the control method of the operation support system 1 of the preferred embodiment, the switching of the joints 21 and 24 having the redundant relationship is automatically performed by the manipulator control unit 76 based on the switching distance L1 calculated by the distance computation unit 75 that constitutes the positional relationship calculation unit. Accordingly, there is no need to perform the switching of the joints 21 and 24 by the operator O who operates the operating unit 41 of the master apparatus 40, a burden to the operator O during the procedure can be reduced, and the procedure can be efficiently performed.

As one of the joints that constitute the slave manipulator 11A is fixed, the inverse kinematics calculation needed for controlling the slave manipulator 11A can be simplified.

When the switching distance L1 is the threshold or less, the joint 24 is fixed and the joint 21 is driven. For this reason, when a relatively small operation such as the needle-hooking operation is performed, contact of the joints other than the joint 21 with surrounding tissues or the like can be suppressed. Then, an operation performance of the operation support system 1 can be improved. Meanwhile, when the switching distance L1 is larger than the threshold, the joint 21 is fixed and the joint 24 is driven. Accordingly, a relatively large operation can be easily performed.

The positional relationship calculation unit includes an image capturing unit detection unit and a treatment unit detection unit. The image capturing unit detection unit can precisely detect the position and the orientation of the distal end section of the endoscope 31 using a shape dimension of the encoders 21b to 27b, and the slave manipulator 11B or the endoscope 31. Since the treatment unit detection unit also has the same configuration as the image capturing unit detection unit, the position of the distal end section of the forceps 30 can be precisely detected.

Since the operation support system 1 includes the endoscope 31 attached to the distal end 11b of the slave manipulator 11B, the operation support system 1 may include all configurations including also the endoscope 31.

The distance computation unit 75 calculates the switching distance L1 only when the forceps 30 is disposed in the field of vision R1 of the endoscope 31. Accordingly, a calculation processing amount of the distance computation unit 75 can be reduced.

Second Preferred Embodiment

Next, while a second preferred embodiment of the present invention will be described with reference to FIGS. 9 and 10, the same components as the above-mentioned preferred embodiment are designated by the same reference numerals and detailed description will be omitted while describing only different points.

Figure 9:
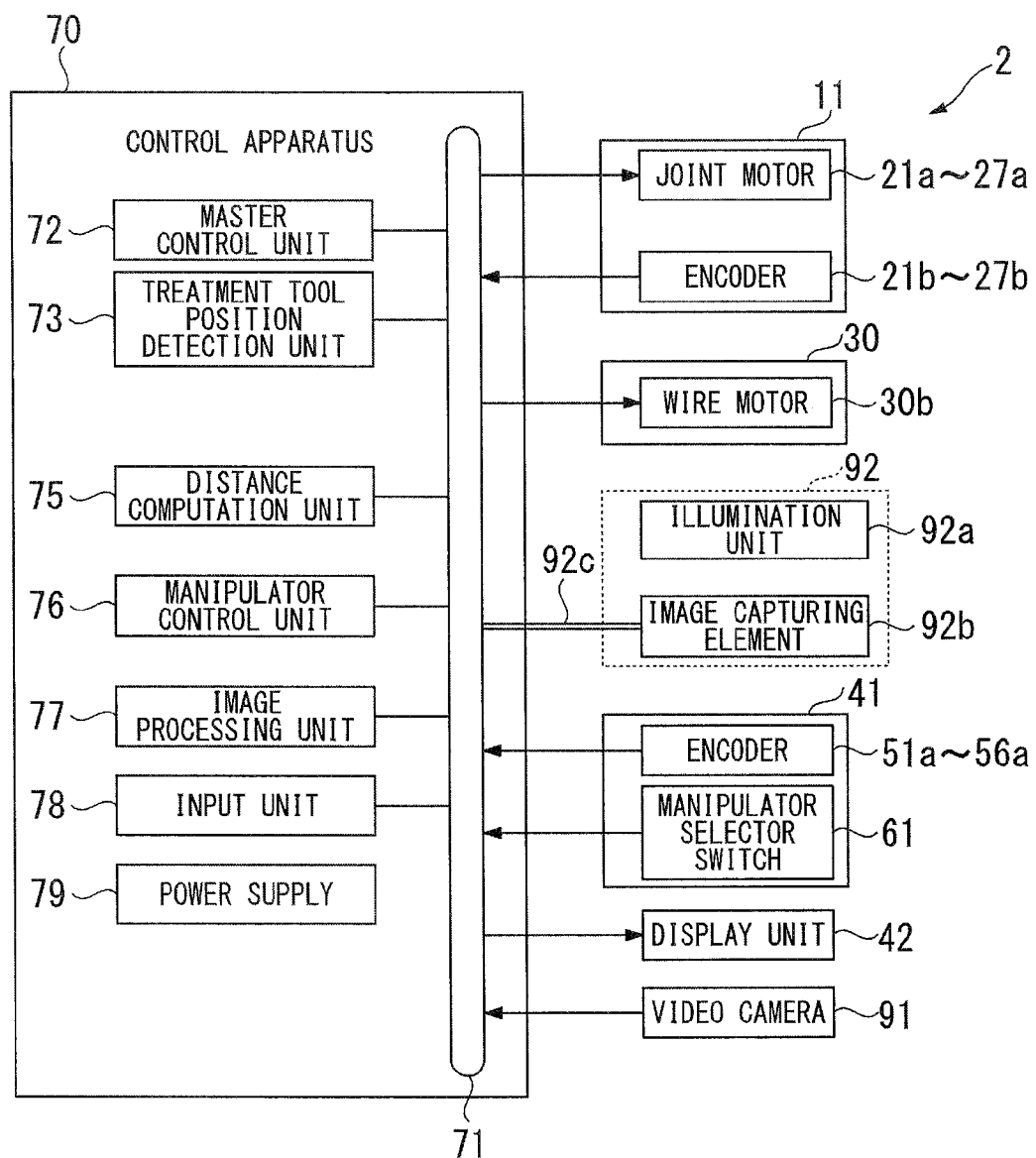
FIG. 9 is a block diagram showing an operation support system in accordance with a second preferred embodiment of the present invention.

As shown in FIG. 9, an operation support system 2 of the preferred embodiment includes a video camera (an image capturing unit detection unit) 91 instead of the endoscope 31 and the endoscope position detection unit 74, with respect to the components of the operation support system 1 of the first preferred embodiment. The operation support system 2 can be connected to a conventional endoscope 92. That is, the operation support system 2 not including the endoscope may be combined with the conventional endoscope 92 and used.

Figure 10:
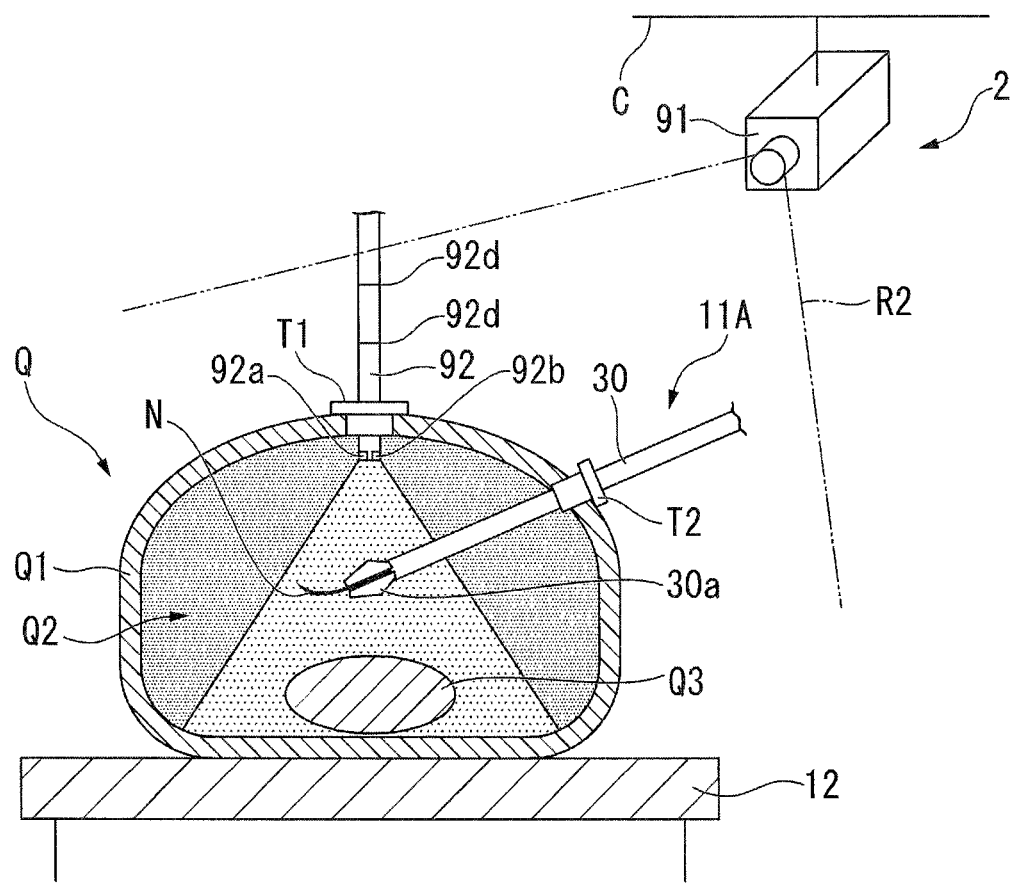
FIG. 10 is a view for describing a procedure using an operation support system in accordance with the second preferred embodiment of the present invention.

As shown in FIG. 10, the video camera 91 may be hung from a ceiling C of an operating room. The video camera 91 is installed such that the endoscope 92 during the procedure enters a field of vision R2. A detection circuit (not shown) is installed in the video camera 91. The detection circuit has a computing device or a memory. When a length of the endoscope 92 connected to the operation support system 2, disposition of the field of vision R2 in the endoscope 92, and so on, are input from the operating unit 41 or the input unit 78, the length, the disposition, and so on, are stored in the memory.

The detection circuit can detect the position and the orientation of the distal end section of the endoscope 92 from the image acquired by the video camera 91 through known image processing. The video camera 91 is connected to the bus 71 of the control apparatus 70 shown in FIG. 9, and the detected position and orientation of the distal end section of the endoscope 92 can be output to the control apparatus 70.

The endoscope 92 may use a known conventional configuration. The endoscope 92 includes, for example, an illumination unit 92a having an LED or the like, and an image capturing element 92b having a CCD or the like. For example, the endoscope 92 is fixed to the operating table 12 or held by the assistant during the procedure.

The image acquired by the image capturing element 92b is output to the image processing unit 77 via a cable 92c that can be connected to the bus 71 of the control apparatus 70, and the image is displayed on the display unit 42.

As an example of a method of detecting the position and the orientation of the distal end section of the endoscope 92, the following method is known. That is, as shown in FIG. 10, a plurality of markers 92d are installed along the entire circumference of the endoscope 92. A distance at which the neighboring markers 92d are spaced apart from each other is previously stored in the detection circuit. As the positions of the plurality of markers 92d are detected by the image processing method, the position and the orientation of the distal end section of the endoscope 92 are detected.

According to the operation support system 2 of the preferred embodiment having the above-mentioned configuration, since the switching of the joints 21 and 24 having the redundant relationship is automatically performed by the manipulator control unit 76, the burden to the operator O during the procedure can be reduced.

Since the operation support system 2 does not include the endoscope and can be connected to the conventional endoscope 92, the conventional endoscope 92 can be effectively utilized and manufacturing cost of the operation support system 2 can be suppressed. When the endoscope with which the operator O or the assistant is familiar is provided, the operation support system 2 can be connected to the endoscope and used. Even in this way, operation performance of the operator O or the assistant can be improved.

In the preferred embodiment, the video camera 91 is hung from a ceiling C. However, disposition of the video camera 91 is not limited thereto, and for example, the video camera 91 may be fixed to the operating table 12 or the assistant may hold the video camera 91.

Third Preferred Embodiment

Next, while a third preferred embodiment of the present invention will be described with reference to FIGS. 11 to 13, the same components as the above-mentioned preferred embodiment are designated by the same reference numerals and detailed description will be omitted while describing only different points.

Figure 11:
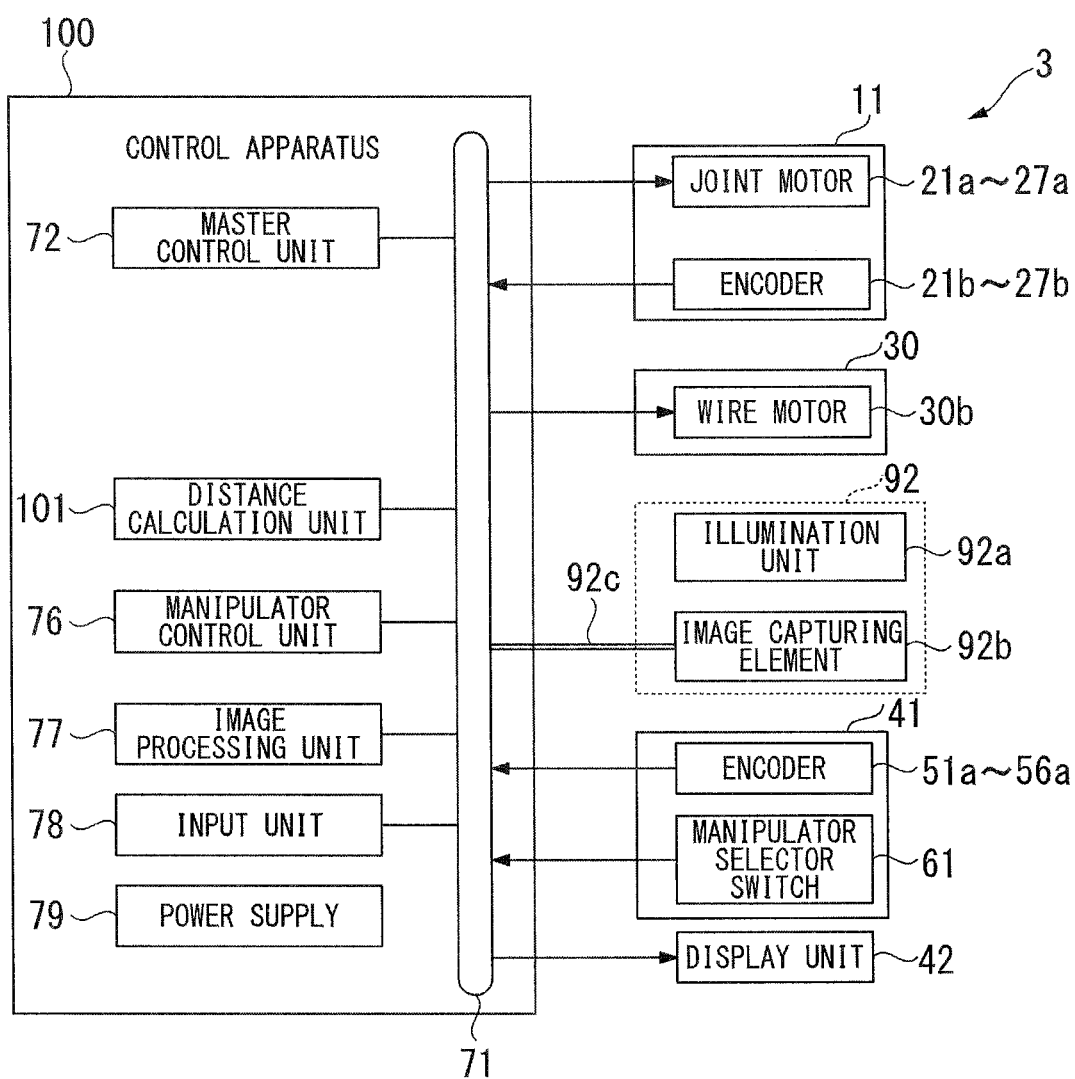
FIG. 11 is a block diagram showing an operation support system in accordance with a third preferred embodiment of the present invention.

As shown in FIG. 11, an operation support system 3 of the preferred embodiment includes a control apparatus 100 instead of the endoscope 31 and the control apparatus 70, with respect to the components of the operation support system 1 of the first preferred embodiment.

The operation support system 3 can be connected to the conventional endoscope 92, like the operation support system 2 of the second preferred embodiment.

The control apparatus 100 includes a distance calculation unit (a positional relationship calculation unit) 101 instead of the treatment tool position detection unit 73, the endoscope position detection unit 74, and the distance computation unit 75, with respect to the components of the control apparatus 70 of the first preferred embodiment.

The distance calculation unit 101 can calculate a distance between the distal end section of the forceps 30 and the distal end section of the endoscope 92 as a switching distance (a switching positional relationship) from the image formed by photographing the forceps 30 and acquired by the endoscope 92 using a known image processing method. In the operation support systems 1 and 2 of the above-mentioned preferred embodiments, the position of the endoscope and the position of the forceps 30 are detected to calculate the switching distance. On the other hand, the distance calculation unit 101 of the preferred embodiment directly calculates the switching distance from the above-mentioned image.

While the image processing method used for calculation of the switching distance is not particularly limited to a known method, the following method may be used.

Figure 12:
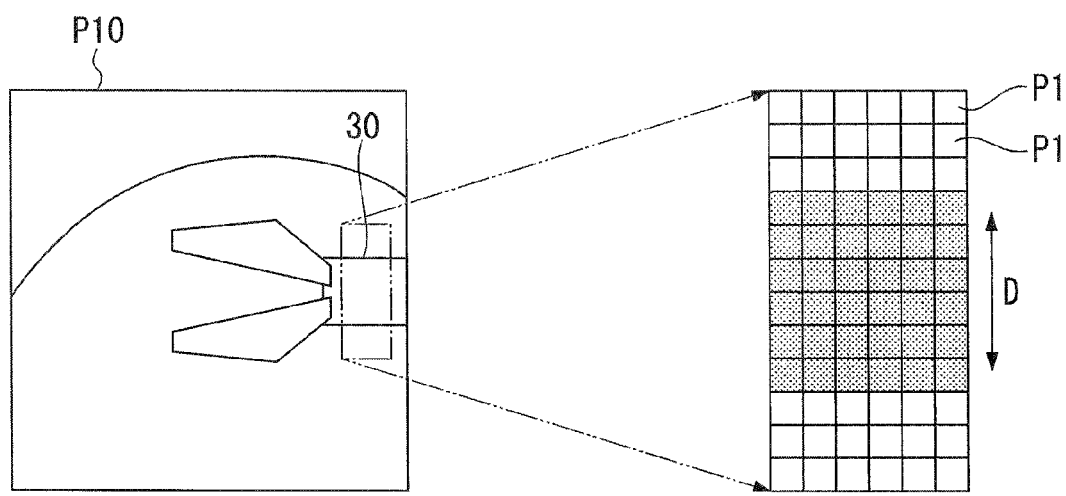
FIG. 12 is a view showing an image when a forceps is disposed relatively close to an endoscope and some of enlarged pixels that constitute the image.
Figure 13:
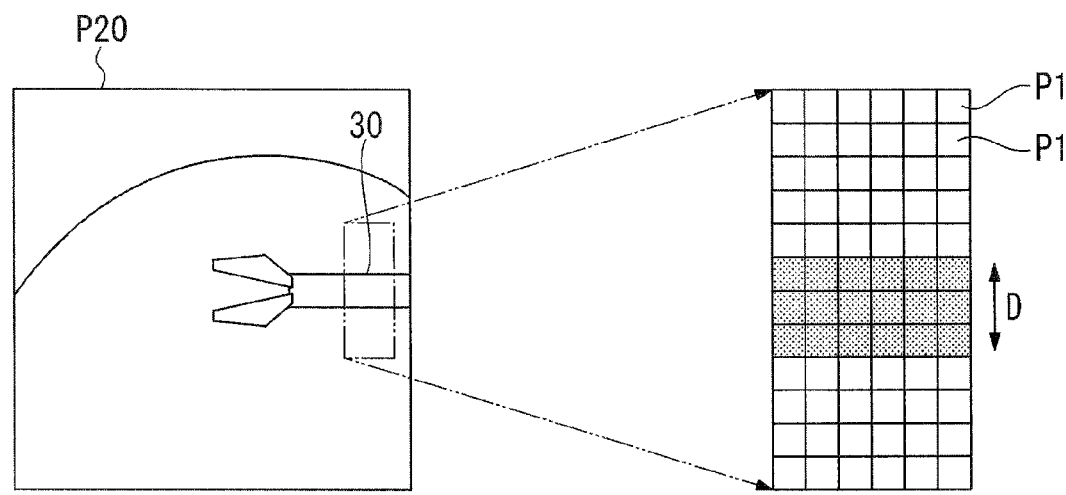
FIG. 13 is a view showing an image when a forceps is disposed relatively far from an endoscope and some of enlarged pixels that constitute the image.

FIGS. 12 and 13 show images P10 and P20 obtained by photographing the forceps 30. The image P10 is acquired by disposing the distal end section of the forceps 30 at a place relatively near the distal end section of the endoscope 92, and the image P20 is acquired by disposing the distal end section of the forceps 30 at a place relatively far from the distal end section of the endoscope 92. These images P10 and P20 are displayed as disposition in which the plurality of pixels P1 are disposed in a lattice shape on a reference plane as partially enlarged in each drawing.

The forceps 30 is photographed small in the image to an image level acquired by disposing the forceps 30 at a place far from the endoscope 92.

The distance calculation unit 101 recognizes a radial direction D of the forceps 30 formed in a rod shape in each of the images P10 and P20 through the known image processing method. A mark that represents a direction may be installed at an outer surface of the forceps 30 such that the distance calculation unit 101 can easily recognize the radial direction D of the forceps 30 in the images P10 and P20.

The distance calculation unit 101 calculates the number of pixels P1 representing the radial direction D and an outer diameter of the treatment unit 30 in the images P10 and P20. The number of pixels P1 is 6 in an example of FIG. 12, or 3 in an example of FIG. 13.

In addition, a table representing correspondence of the number of pixels P1 and the switching distance is previously stored in the memory of the distance calculation unit 101. The distance calculation unit 101 calculates the switching distance based on the table.

According to the operation support system 3 of the preferred embodiment having the above-mentioned configuration, the switching of the joints 21 and 24 having the redundant relationship can be automatically performed.

When the switching distance is relatively small and the forceps 30 and the endoscope 92 are closely disposed, since the joints 21 to 27 are controlled not to be unnecessarily operated, the forceps 30 is prevented from coming in contact with the endoscope 92. In addition, when the switching distance is relatively large and the forceps 30 and the endoscope 92 are disposed far from each other, there is no problem even when the slave manipulator 11A is largely operated.

Fourth Preferred Embodiment

Next, while a fourth preferred embodiment of the present invention will be described with reference to FIGS. 14 to 16, the same components as the above-mentioned preferred embodiment are designated by the same reference numerals and detailed description will be omitted while describing only different points.

Figure 14:
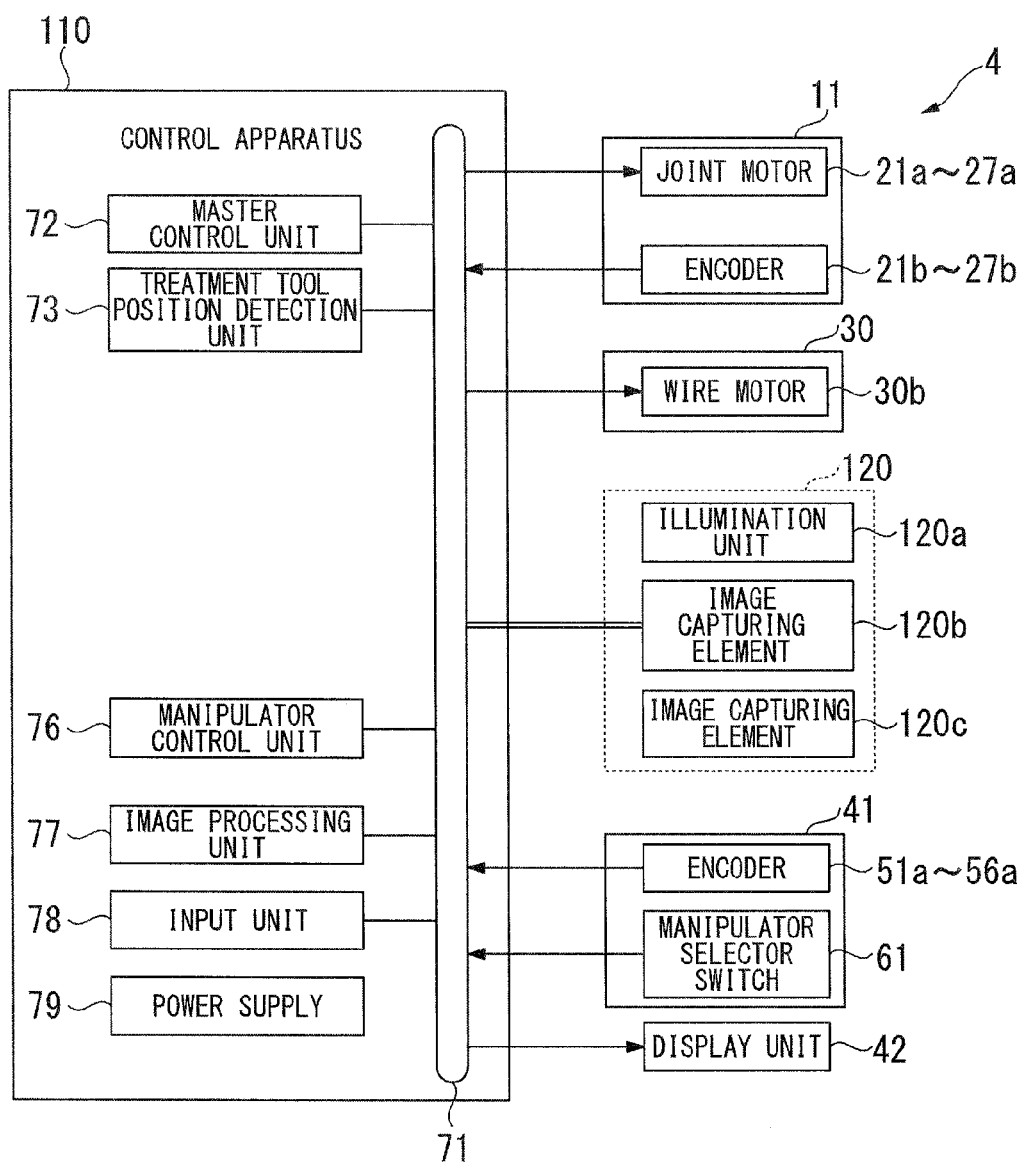
FIG. 14 is a block diagram showing an operation support system in accordance with a fourth preferred embodiment of the present invention.

As shown in FIG. 14, an operation support system 4 of the preferred embodiment includes a control apparatus 110 instead of the endoscope 31 and the control apparatus 70, with respect to the components of the operation support system 1 of the first preferred embodiment.

Figure 15:
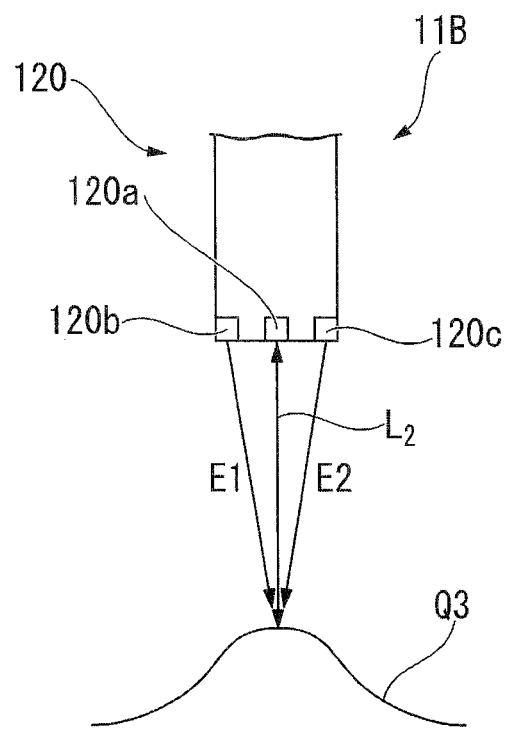
FIG. 15 is a view showing an endoscope used with the operation support system in accordance with the fourth preferred embodiment of the present invention.
Figure 16:
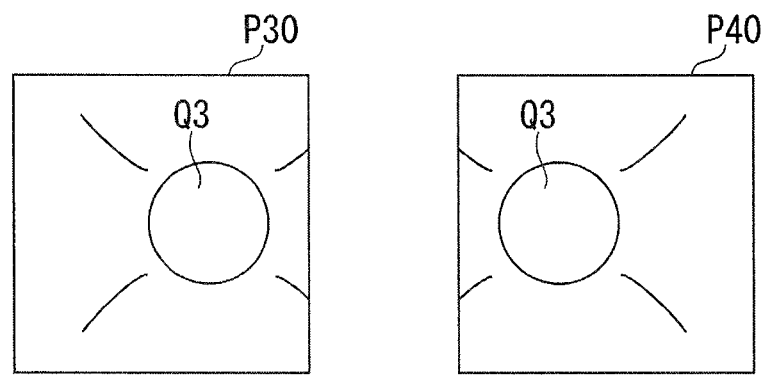
FIG. 16 is a view showing an example of a first image and a second image acquired by the endoscope in accordance with the fourth preferred embodiment of the present invention.

As shown in FIGS. 14 and 15, a known endoscope 120 configured to measure a distance can be connected to the operation support system 4. That is, in the preferred embodiment, the endoscope 120 functions as a distance calculation unit (a positional relationship calculation unit).

The endoscope 120 includes an illumination unit 120a having an LED or the like installed at a distal end section thereof, and a pair of image capturing elements 120b and 120c such as CCDs or the like.

The image capturing element 120b can acquire a first image P30 (see FIG. 16) obtained by photographing the target tissue Q3 in a direction E1. Meanwhile, the image capturing element 120c can acquire a second image P40 (see FIG. 16) obtained by photographing the target tissue Q3 in a direction E2. These directions E1 and E2 are different from and oblique to each other. That is, as the first image P30 and the second image P40 are simultaneously acquired, for example, the first image P30 displayed on the display unit 42 is seen with a right eye and the second image P40 is seen with a left eye, the operator O can 3-dimensionally observe the target tissue Q3 on the display unit 42.

In addition, a detection circuit (not shown) is installed in the endoscope 120. The detection circuit has a computing device or a memory. The detection circuit can calculate a distance between the target tissue Q3 and the distal end section of the endoscope 120 as a switching distance (a switching positional relationship) L2 based on the first image P30 and the second image P40 acquired by the image capturing elements 120b and 120c through the known image processing method. That is, in the preferred embodiment, the switching distance L2 is calculated based on parallax between the first image P30 and the second image P40.

In addition, the control apparatus 110 does not include the treatment tool position detection unit 73, the endoscope position detection unit 74, and the distance computation unit 75, with respect to the components of the control apparatus 70 of the first preferred embodiment.

According to the operation support system 4 of the preferred embodiment having the above-mentioned configuration, the switching of the joints 21 and 24 having the redundant relationship can be automatically performed.

When the switching distance L2 is relatively small and the target tissue Q3 and the endoscope 120 are closely disposed, since the joints 21 to 27 are controlled not to be unnecessarily operated, the endoscope 120 is prevented from coming in contact with the target tissue Q3. In addition, when the switching distance L2 is relatively large and the target tissue Q3 and the endoscope 120 are spaced apart from each other, there is no problem even when the slave manipulator 11B is largely operated.

In addition, in the preferred embodiment, the switching distance L2 was calculated as a distance between the target tissue Q3 and the distal end section of the endoscope 120 based on parallax between the first image P30 and the second image P40. However, the calculation method of the switching distance L2 is not limited thereto. For example, the switching distance L2 may be calculated using an arrival time of an ultrasonic wave, a laser beam, or the like, or a variation in wavelength.

Hereinabove, while the first preferred embodiment to the fourth preferred embodiment of the present invention have been described with reference to the accompanying drawings, specific configurations are not limited to the preferred embodiments but may include variations in configurations without departing from the scope of the present invention. Further, it is needless to say that the configurations shown in the preferred embodiments can be appropriately combined and used.

For example, in the first preferred embodiment to the fourth preferred embodiment, the treatment unit was the forceps 30. As the treatment unit, in addition to this, a snare, a syringe, a high frequency treatment tool, or the like, may be appropriately selected and used.

In addition, in the slave manipulator 11 having the seven joints 21 to 27, the joints 22 and 24 in which the motion shafts are the rotary shafts have the redundant relationship. However, the slave manipulator may have eight joints or more, and joints other than the six joints among the eight or more joints may have the redundant relationship. In this case, when one or more of the plurality of joints having the redundant relationship are automatically selected and fixed, the same effect as the preferred embodiment is exhibited. In addition, two or more joints in which the motion shafts are linear moving shafts may have the redundant relationship. The slave manipulator may have six or fewer joints and two or more of these joints may have the redundant relationship.

The slave manipulator 11 may include three or more redundant joints having the redundant relationship. In this case, the manipulator control unit 76 selects and drives one of the three or more redundant joints based on the switching distance L1, and fixes the remaining redundant joint.

In the third and fourth preferred embodiments, even when an image is acquired by a reflected light passing through a zoom lens, if a magnification of the zoom lens can be detected, the switching distance can be calculated in consideration of the magnification.

The number of the slave manipulators 11 included in the operation support system is not limited, and at least one slave manipulator 11A may be provided.

The operating unit may not be electrically connected to the control apparatus through a wiring or the like, and the operating unit and the control apparatus may be connected through wireless communication. In this case, as the operator O who grips the operating unit moves or rotates the operating unit in a 3-dimensional space, the operation signal corresponding to 3 degrees of freedom of the position can be output to the control apparatus.

In the first and second preferred embodiments, the endoscope may be fixed, and the position and the orientation of the endoscope are input from the input unit 78 to be stored in the distance computation unit 75 or the like. In this case, as the position of the distal end section of the forceps 30 can be detected every moment, the switching distance can be calculated.

Figure 17:
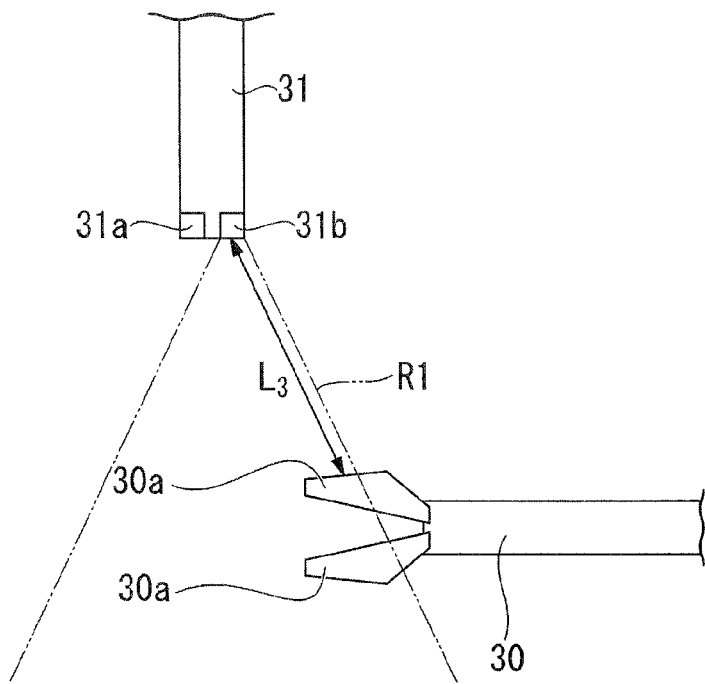
FIG. 17 is a view for describing another example of a switching distance measured by a control apparatus of the operation support system in accordance with the fourth preferred embodiment of the present invention.

In the first preferred embodiment, a distance between the distal end section of the forceps 30 and the distal end section of the endoscope 31 along a central axis of the field of vision R1 was calculated as the switching distance L1. However, as shown in FIG. 17, when the distal end section of the forceps 30 is disposed at an edge of the field of vision R1, a distance between the distal end section of the forceps 30 and the distal end section of the endoscope 31 along the edge of the field of vision R1 may be calculated as a switching distance L3.

Figure 18:
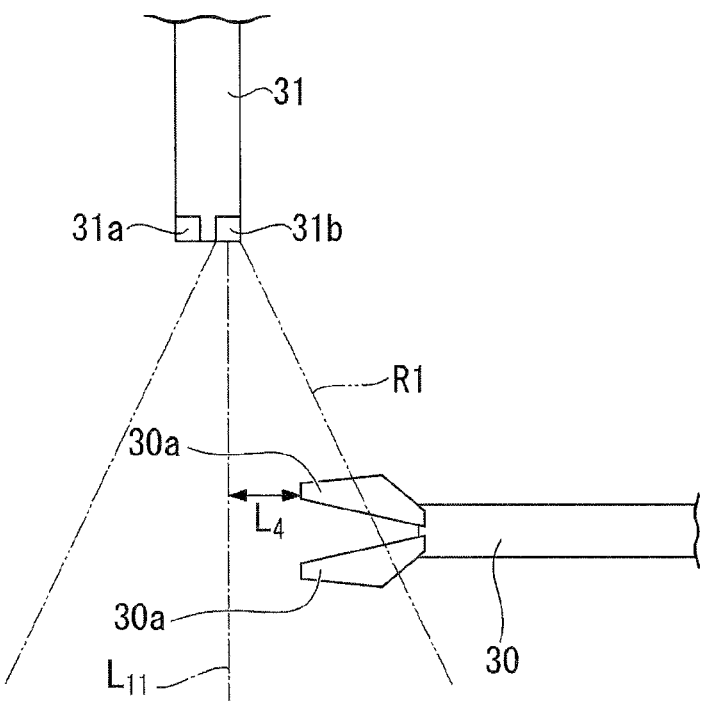
FIG. 18 is a view for describing another example of the switching distance measured by the control apparatus of the operation support system in accordance with the fourth preferred embodiment of the present invention.

In addition, as shown in FIG. 18, a distance from a central axis L11 of the field of vision R1 spread in a substantially conical shape to the distal end section of the forceps 30 may be the switching distance L4.

Furthermore, the present invention is not limited to the above-mentioned description but limited only to the scope of the accompanying claims.

What is claimed is:

1. An operation support system configured to perform treatment on a target tissue, which is a treatment target, while observing by using an image sensor, using a treatment device installed at a distal end side of a slave manipulator, which is a distal end when seen from a fixing end of the slave manipulator, the operation support system comprising:
the slave manipulator having a plurality of joints corresponding to a plurality of degrees of freedom and including at least two redundant joints having a redundant relationship among the plurality of joints;
a master manipulator configured to provide operating information corresponding to the plurality of degrees of freedom; and
a controller configured to:
calculate a switching positional relationship between the target tissue or the treatment device and the image sensor; and
control an operation of each of the plurality of joints according to the operating information,
wherein the controller controls the slave manipulator using one of the at least two redundant joints as a driving joint and an other of the at least two redundant joints as a fixing joint based on the switching positional relationship.

2. The operation support system according to claim 1, wherein the switching positional relationship represents a distance between the target tissue or the treatment device and the image sensor, and
the controller uses a joint closest to a distal end of the slave manipulator of the at least two redundant joints as the driving joint when the switching positional relationship is equal to or less than a threshold, and
the controller uses a joint farthest from the distal end of the slave manipulator of the at least two redundant joints as the driving joint when the switching positional relationship is larger than the threshold.

3. The operation support system according to claim 1, wherein the controller is further configured to:
detect a position of the image sensor;
detect a position of the treatment device, and
calculate a distance between the treatment device and the image sensor as the switching positional relationship based on the detected position of the image sensor and the detected position of the treatment device.

4. The operation support system according to claim 3, further comprising the image sensor capable of acquiring an image.

5. The operation support system according to claim 3, wherein the controller is configured to calculate the distance only when the treatment device is disposed in a field of vision of the image sensor.

6. The operation support system according to claim 1, wherein the controller is configured to calculate a distance between the treatment device and the image sensor as the switching positional relationship based on an image obtained by photographing the treatment device and acquired by the image sensor.

7. The operation support system according to claim 1, wherein the image sensor is capable of acquiring a first image and a second image obtained by photographing the target tissue from different oblique directions, and
the controller is configured to calculate a distance between the target tissue and the image sensor as the switching position relationship based on the acquired first and second images.

8. A control method of an operation support system configured to control the operation support system including a slave manipulator having a plurality of joints corresponding to a plurality of degrees of freedom and including at least two redundant joints having a redundant relationship among the plurality of joints, the control method comprising:
calculating a switching positional relationship between a target tissue treated using a treatment device installed at the slave manipulator or the treatment device and an image sensor; and
controlling the slave manipulator based on the switching positional relationship using one of the at least two redundant joints as a driving joint and an other of the at least two redundant joints as a fixing joint.

9. The control method according to claim 8, wherein the switching positional relationship represents a distance between the target tissue or the treatment device and the image sensor, and
the control method further comprises controlling the slave manipulator based on the switching positional relationship using a joint closest to a distal end of the manipulator of the at least two redundant joints as the driving joint when the switching positional relationship is equal to or less than a threshold, and using a joint farthest from the distal end of the manipulator of the at least two redundant joints as the driving joint when the switching positional relationship is larger than the threshold.

10. The control method according to claim 8, wherein the calculating of the switching positional relationship comprises:
- detecting a position of the image sensor;
- detecting a position of the treatment device; and
- calculating a distance between the treatment device and the image sensor as the switching positional relationship based on the position of the image sensor and the position of the treatment device.

11. The control method according to claim 10, wherein the calculating of the distance is performed only when the treatment device is disposed in a field of vision of the image sensor.

12. The control method according to claim 8, wherein the calculating of the switching positional relationship comprises calculating a distance between the treatment device and the image sensor as the switching positional relationship based on an image obtained by photographing the treatment device and acquired by the image sensor.

13. The control method according to claim 8, further comprising acquiring a first image and a second image obtained by photographing the target tissue from different oblique directions,
wherein the calculating of the switching positional relationship includes calculating a distance between the target tissue and the image sensor as the switching positional relationship based on the acquired first and second images.

* * * * *